(12) United States Patent
Bonacini et al.

(10) Patent No.: US 9,714,899 B2
(45) Date of Patent: Jul. 25, 2017

(54) METHOD FOR MONITORING A CONTROL PARAMETER OF A POLYMERIZATION REACTION AND RELATIVE APPARATUS FOR IMPLEMENTING SAID METHOD

(71) Applicant: versalis S.p.A., San Donato Milanese (IT)

(72) Inventors: Francesco Bonacini, Mantova (IT); Erik Mantovani, Revere (IT); Angelo Ferrando, Sestri Levante (IT)

(73) Assignee: versalis S.p.A., San Donato Milanese (IT)

( * ) Notice: Subject to any disclaimer, the term of this patent is extended or adjusted under 35 U.S.C. 154(b) by 0 days.

(21) Appl. No.: 15/027,179

(22) PCT Filed: Nov. 18, 2014

(86) PCT No.: PCT/IB2014/066129
§ 371 (c)(1),
(2) Date: Apr. 4, 2016

(87) PCT Pub. No.: WO2015/075629
PCT Pub. Date: May 28, 2015

(65) Prior Publication Data
US 2016/0231230 A1 Aug. 11, 2016

(30) Foreign Application Priority Data
Nov. 19, 2013 (IT) .............................. MI2013A1916

(51) Int. Cl.
*C08F 2/00* (2006.01)
*C08F 4/00* (2006.01)
(Continued)

(52) U.S. Cl.
CPC .......... *G01N 21/272* (2013.01); *C08F 112/08* (2013.01); *G01N 21/359* (2013.01);
(Continued)

(58) Field of Classification Search
CPC ............. G01N 21/3577; G01N 21/359; G01N 21/8507; G01N 21/272; G01N 2201/13; G01N 2201/061; G01N 2201/0826
(Continued)

(56) References Cited

U.S. PATENT DOCUMENTS 5,898,056 A * 4/1999 Josephy ............... B01J 19/0006
524/834
6,864,331 B1 * 3/2005 Reimers ............... B01J 19/0006
356/319

(Continued)

OTHER PUBLICATIONS

International Search Report issued Jan. 20, 2015 in PCT/IB2014/066129.

*Primary Examiner* — William Cheung
(74) *Attorney, Agent, or Firm* — Oblon, McClelland, Maier & Neustadt, L.L.P.

(57) ABSTRACT

The present invention relates to a method for monitoring a control parameter of a polymerization reaction mixture in heterogeneous phase comprising the following steps: (a) acquiring at least one NIR reflectance spectrum of said mixture; (b) calculating a value of said control parameter by means of a calibration curve which correlates the NIR reflectance spectrum with the values of said control parameter measured with a reference measurement method. The present invention also relates to an apparatus for implementing said method.

13 Claims, 4 Drawing Sheets

(51) Int. Cl.
    *C08F 12/02*      (2006.01)
    *G01N 21/27*      (2006.01)
    *G01N 21/3577*    (2014.01)
    *G01N 21/359*     (2014.01)
    *G01N 21/85*      (2006.01)
    *C08F 112/08*     (2006.01)

(52) U.S. Cl.
    CPC ..... *G01N 21/3577* (2013.01); *G01N 21/8507* (2013.01); *G01N 2201/061* (2013.01); *G01N 2201/0826* (2013.01); *G01N 2201/13* (2013.01)

(58) Field of Classification Search
    USPC .................................... 526/59, 72, 91, 346
    See application file for complete search history.

(56) References Cited

U.S. PATENT DOCUMENTS

| | | |
|---|---|---|
| 2002/0082383 A1 | 6/2002 | Kurose et al. |
| 2012/0203472 A1* | 8/2012 | Lacombe ............. G01N 21/274 702/30 |

* cited by examiner

METHOD FOR MONITORING A CONTROL PARAMETER OF A POLYMERIZATION REACTION AND RELATIVE APPARATUS FOR IMPLEMENTING SAID METHOD

RELATED APPLICATIONS

This application is a National Stage Entry of International Application No. PCT/IB14/66129, filed Nov. 18, 2014, and claims the benefit of and priority to Italy Application No. MI2013A001916, filed Nov. 19, 2013, all of which are incorporated herein by reference in their entirety.

The present invention relates to a method for monitoring a control parameter of a polymerization reaction and the relative apparatus for implementing said method.

As is known, in processes for the industrial production of polymers, the possibility of continuously controlling the conditions at which the polymerization reaction takes place in order to obtain a high-quality product and high production yields, in addition to guaranteeing the management of the production plant under safety conditions, is of fundamental importance.

The control of an industrial polymerization process is generally based on the monitoring of some physical and chemical parameters of the reaction mixture, such as for example, the temperature and pressure inside the reactor, and the state of progress of the reaction.

In the case, for example, of the suspension synthesis of expandable polystyrene (EPS), the most important control parameters to be monitored include the size of the particles or beads of polymer which are formed and grow as the reaction proceeds and the conversion degree of the styrene monomer into polymer.

Various techniques and devices are available in the state of the art, which allow the control parameters of polymerization reactions to be accurately monitored.

Among these, in particular, monitoring techniques based on Near Infrared Spectroscopy (NIR) are receiving increasing attention, as they allow the above parameters to be rapidly and precisely measured in-line, i.e. directly on the reaction mixture inside the reactor.

In-line measurement devices based on NIR spectroscopy generally comprise a measurement probe connected by means of optical fibers to a light source and to a spectrophotometer. The probe is housed in the reactor, with the measurement head immersed in the polymerization mixture. The measurement head comprises a cavity inside which the polymerization mixture subjected to analysis flows. During the measurement, the probe irradiates the polymerization mixture through a window transparent to NIR radiation (sampling window) present in the measurement cavity, with a light radiation having a wavelength in the near infrared (incident radiation) produced by the light source and, at the same time, collects the light radiation scattered by the reaction mixture—created by the effect of irradiation with the incident radiation—sending it to the spectrophotometer.

In the technical field of the present invention, NIR spectroscopy is substantially applied in so-called "transmittance" or "in transflectance" modes.

In transmittance spectroscopy, the radiation analyzed by the spectrophotometer is the fraction of incident radiation that passes through the sample, i.e. the fraction which is neither absorbed nor reflected thereby.

In "in transflectance" spectroscopy, the radiation analyzed by the spectrophotometer is the fraction of incident radiation which, after passing through the sample, is reflected by a specific reflecting screen situated in the measurement cavity along the pathway of the radiation, beyond the sample; the radiation reflected by the screen passes through the sample a second time, before reaching the spectrophotometer.

By means of chemometric calibration methods, the absorption characteristics of a NIR spectrum of a polymerization mixture can be correlated with the desired control parameter (e.g. average size of the polymer particles or conversion degree of the starting monomer), obtaining a predictive mathematical model of the control parameter. After an appropriate validation of the calibration method, the predictive model can be used for estimating the value of the control parameter of a polymerization mixture from a NIR spectrum measured on it in-line.

The monitoring methods of control parameters of polymerization reactions in heterogeneous phase by means of NIR spectroscopy known in the art have various critical aspects.

In these reactions, the polymerization mixture tends to stick to the sampling window of the immersion probe due to its highly viscous nature. A residue of material consequently accumulates on the window as the reaction proceeds, which interferes with the measurement, preventing the correct determination of the control parameter. The fouling of the sampling windows therefore requires frequent stoppages of the plant to allow cleaning or substitution of the probe.

NIR probes, moreover, generally consist of a metallic body having an elongated form which is inserted in a wall of the reactor so that the measurement head remains constantly immersed in the polymerization mixture. The body of the probe extends from the wall of the reactor towards its interior, in some cases protruding as far as a distance of approximately 20 centimeters. Consequently the probe, with its dimensions, affects the fluid-dynamics of the polymerization reaction.

An example of the use of transmittance NIR spectroscopy for the in-line monitoring of the control parameters of the synthesis of polystyrene in aqueous suspension and the critical aspects indicated above, is described in A. F. Santos et al., Journal of Applied Polymer Science, Vol. 70, 1737-1745 (1998).

The drawbacks of in-line measurements can be partially overcome by using NIR measurement systems operating on-line. In on-line measurement systems, the sample to be analyzed is removed, either continuously or discontinuously, from the reactor during the polymerization reaction and transferred to the measurement instrument through a transfer line. In on-line measurements, the absence of a probe immersed in the polymerization mixture, however, does not eliminate the problem of fouling of the sampling windows, as the polymerization mixture must in any case pass into a measurement cell (positioned outside the reactor and connected to this through a transfer line) with problems completely analogous to those of the measurement cavities of immersion probes. Furthermore, in many cases, during the transfer of the sample of the reaction mixture from the reactor to the measurement instrument, there may be a structural alteration in the sample itself, which can also significantly influence the result of the determination of the control parameter (for example, coalescence phenomena of the particles may arise with a consequent overestimation of the real dimensions of the particles of the polymerization mixture).

The critical aspects illustrated above have so far prevented an adequate exploitation of the potentiality of NIR spectroscopy in the monitoring of control parameters of polymerization reactions in heterogeneous phase. In the case of the synthesis of EPS, for example, in the light of the drawbacks discussed above, the use of evaluation methods of the average size of polymer beads during the reaction, based on visual inspection of the polymerization mixture on the part of an operator or on an analysis of samples of the reaction mixture effected in a laboratory (so-called off-line measurements), is still frequent.

The objective of the present invention is to overcome or at least to reduce the drawbacks of the state of the art indicated above.

Within this general objective, an objective of the present invention is to provide a method for monitoring a control parameter of a polymerization reaction in heterogeneous phase which is reliable, capable of guaranteeing a monitoring of the above parameter also continuously, and which does not require frequent maintenance interventions of the equipment.

In the light of these objectives and others that will appear more evident hereunder, according to a first aspect, the present invention relates to a method for monitoring a control parameter of a polymerization reaction mixture in heterogeneous phase comprising the following steps:

(a) acquiring at least one NIR reflectance spectrum of said mixture;

(b) calculating a value of said control parameter by means of a calibration curve which correlates the NIR reflectance spectrum with the values of said control parameter measured with a reference measurement method.

According to a second aspect, the present invention relates to a control method of a polymerization reaction in heterogeneous phase which comprises the phase of monitoring at least one control parameter of said reaction according to the above-mentioned monitoring method.

According to a further aspect, the present invention relates to an apparatus for implementing the above monitoring method which comprises at least one polymerization reactor equipped with at least one acquisition system of NIR reflectance spectra comprising:

at least one probe for irradiating a light radiation onto a polymerization reaction mixture contained in said reactor and substantially only collecting the radiation reflected from said mixture in response to said irradiation, at least one detection system optically coupled with said probe for detecting said radiation reflected.

The Applicant has surprisingly found that the drawbacks of the state of the art can be overcome using a method for determining the control parameters of a polymerization reaction in heterogeneous phase, wherein the NIR spectra of the polymerization mixture are acquired in reflectance, rather than in transmittance or transflectance. NIR reflectance spectroscopy, frequently used in the state of the art for the characterization of solid surfaces, in fact, allows optical fiber probes to be used, which do not require being immersed in the polymerization mixture to allow the NIR spectra to be acquired in-line, but only require that they be in contact with it.

Thanks to the fact that the probes for NIR reflectance spectroscopy are based on a different spectroscopic analysis procedure with respect to that of probes for transmittance and transflectance spectroscopy, they do not have measurement cavities in which the reaction mixture must flow, and they are consequently much less subject to fouling phenomena. Probes for NIR reflectance spectroscopy, in fact, acquire the spectra through a sampling window which only requires being in contact with the polymerization mixture. These probes can therefore be substantially aligned with the internal wall of the polymerization reactor.

The advantages that can be obtained with the use of the reflectance spectroscopy according to the present invention are even more surprising considering that the intensity of the radiation reflected by the polymerization mixture that can be collected by a probe (and subsequently processed by the detection system) is much lower with respect to what can be collected with transmittance or transflectance measurement probes.

BRIEF DESCRIPTION OF THE DRAWINGS

The method according to the present invention and the relative apparatus for implementing it are described hereunder for a better understanding of the characteristics of the present invention, with reference to the following figures.

Figure 1:
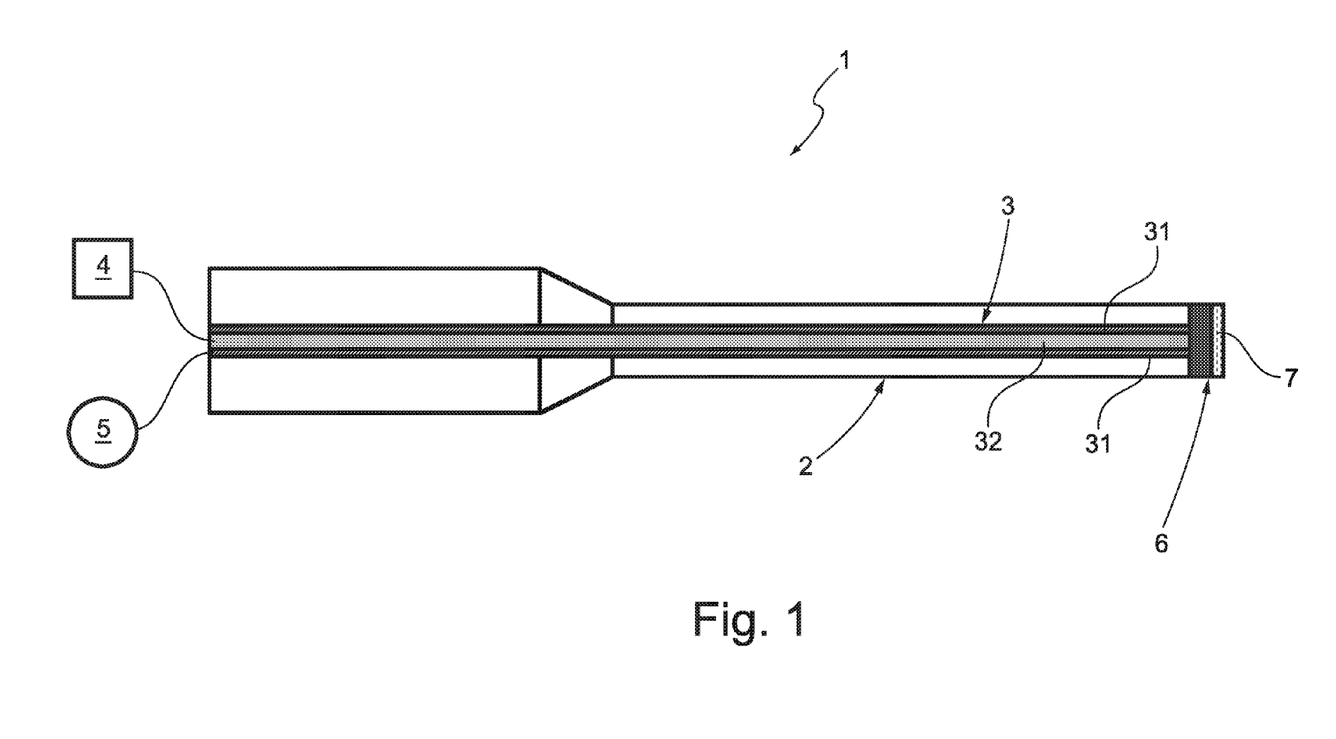
FIG. 1, which shows a schematic representation of a probe for NIR reflectance spectroscopy according to the state of the art, which can be used for the purposes of the present invention.

With reference to FIG. 1, the probe 1 for NIR reflectance spectroscopy comprises a body 2, generally in cylindrical form, in which at least one bundle of optical fibers 3 is housed. The above body 2 is coupled at one end with a measurement head 6, which, in turn, is coupled with a sampling window 7.

A first fraction 32 of said bundle of optical fibers 3, for example those positioned in the internal part of the bundle, is optically connected, at a first end, to a light radiation source 4 (for example a tungsten halogen lamp) and, at a second end, to the sampling window 7. A second fraction 31 of said fibers, for example, that at the outermost part of the bundle 3, is, on the other hand, optically connected, at a first end, to a detection system 5, to which the radiation reflected from the sample due to the irradiation effected with the first fraction of fibers 32, is conveyed, and, at a second end, to the sampling window 7.

In an alternative configuration, the fraction of optical fibers connected to the light radiation source 4 can be at the outermost part of the bundle 3, whereas the fraction of optical fibers that conveys the radiation reflected to the detection system 5, is in the innermost part.

The sampling window 7 is made of a material transparent to light radiation (for example, quartz or sapphire) coming from the light radiation source 4.

When functioning, the probe 1 can irradiate, through the sampling window 7, the light radiation coming from the source 4, through the optical fibers 32, onto a polymerization mixture 8 positioned in a polymerization reactor 9, and, at the same time, substantially collect only the radiation reflected from said mixture 8 in response to said irradiation. The radiation reflected is then sent by means of the optical fibers 31 to the detection system 5, which processes the light signal and sends it to an electronic processor 10 where it can be processed and visualized in the form of a NIR spectrum (for example, an absorption unit spectrum with respect to a wavenumber).

Figure 2:
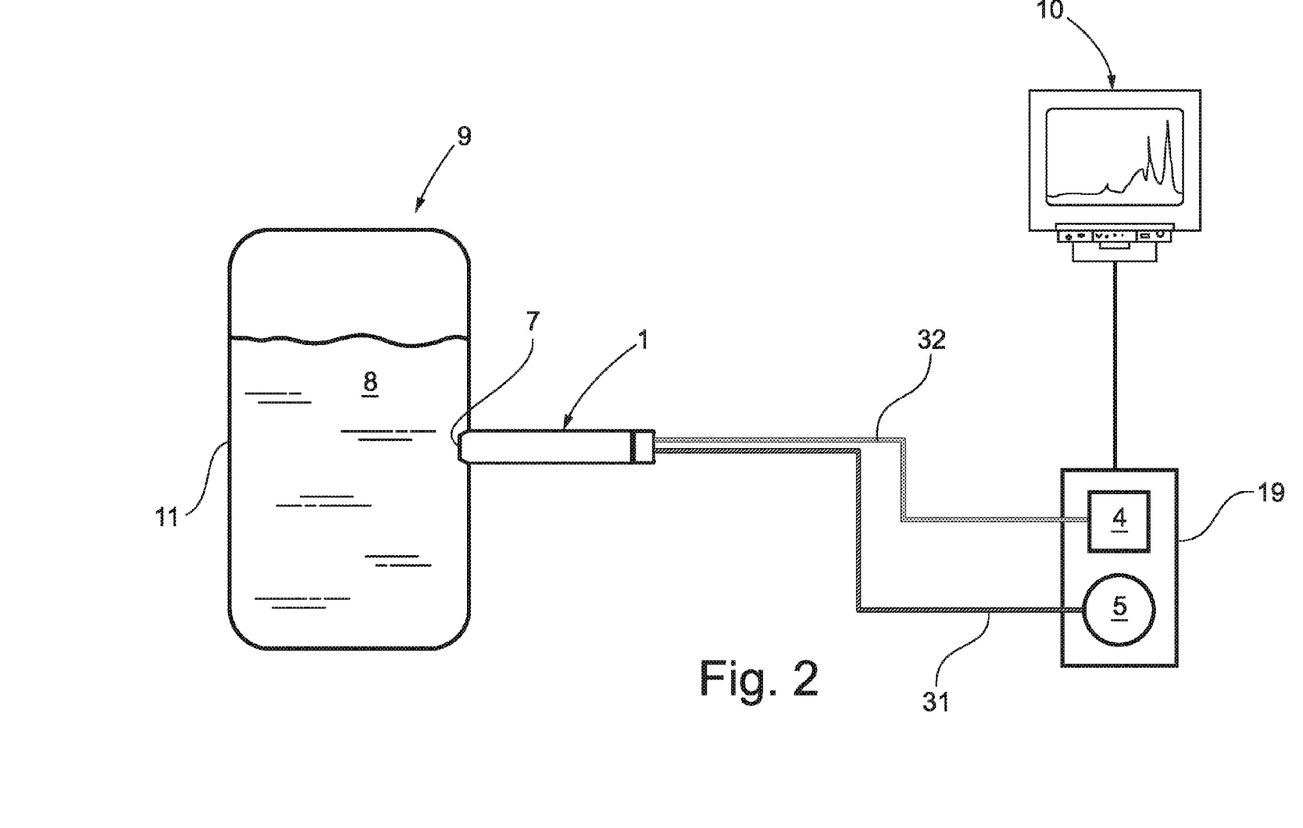
FIG. 2, which shows a schematic representation of an apparatus for implementing the present invention.

The light radiation source 4 and the detection system 5 can be both advantageously housed in a spectrophotometric measurement device 19 (FIG. 2).

The probe 1 is inserted inside the polymerization reactor 9 so that the sampling window 7 is in contact with the polymerization mixture 8. The probe 1 is preferably inserted inside a wall 11 of the reactor 9, in a substantially transversal direction with respect to this. In this configuration, the sampling window 7 is substantially parallel to said wall 11 of the reactor 9. The surface of said window 7 facing the polymerization mixture is also substantially aligned with the internal surface of the wall 11 of the reactor 9. Said surface of said window 7, in fact, protrudes with respect to the surface of the internal wall 11 of the reactor by less than 1 cm, preferably less than 0.5 cm, even more preferably less than 0.2 mm. This arrangement of the probe in addition to guaranteeing a significantly low fouling of the window 7, does not influence the fluid-dynamics of the polymerization reaction inside the reactor 9, as the probe 1 occupies a negligible fraction of the internal volume of the reactor 9.

It cannot be excluded, however, that the probe 1 can be inserted in the reactor 9 also in other configurations (for example, with the measurement head 6 tilted with respect to the wall 11 of the reactor 9), as the absence of a measurement cavity in any case guarantees a limited fouling of the sampling window 7 during the reaction.

With the monitoring method of the present invention, up to a hundred polymerization cycles (batch) can be consecutively effected in the same reactor without having to intervene for cleaning the probe between one cycle and the next.

The method according to the present invention can be used for continuously or discontinuously monitoring the trend of one or more control parameters of a polymerization reaction in heterogeneous phase. The values of the control parameter acquired in the monitoring can be advantageously used for controlling the progress of the reaction and possibly for intervening on the same, for example by modifying the operating parameters of the reactor and/or equipment connected therewith.

The method according to the present invention can be advantageously applied to the monitoring of polymerization reactions of α-olefins having general formula $R_1R_2C=CH_2$, wherein:

$R_1$ is hydrogen or methyl;
$R_2$ is a group selected from: $C_1$-$C_{10}$ alkyl, $C_1$-$C_6$ aryl possibly substituted with one or more groups selected from halogen, $C_1$-$C_4$ alkyl and $C_1$-$C_4$ alkoxyl.

The application of the method according to the present invention to the monitoring of a synthesis reaction of polystyrene, preferably in aqueous suspension, is particularly preferred.

The control parameters that can be monitored with the present method substantially include parameters correlated to the physico-chemical properties of the polymerization mixture that influence the characteristics of its NIR spectrum.

Preferred control parameters are: the average particle size (or diameter) of the polymer formed during the polymerization reaction and the conversion degree of at least one monomer of the polymerization mixture (reference monomer).

In the case of the monitoring of the average particle size, the method is particularly effective for determining the average dimensions of polymer particles within the range of 100 μm-3 mm, preferably 300 μm-1.5 mm. Particles having dimensions within the above range, in fact, cause interference phenomena with the incident light radiation which generate NIR spectra with a reduced background noise.

The invention is further described hereunder with reference to the case of the monitoring of a control parameter of the synthesis reaction of expandable polystyrene (EPS) in aqueous suspension, in particular the monitoring of the dimensions of polymer particles formed during the reaction. This embodiment should in any case be considered as being a preferred and non-limiting embodiment of the application scope of the invention.

The synthesis reaction of EPS is a radical polymerization reaction of styrene. The reaction is generally carried out at a temperature within the range of 80-200° C. in the presence of one or more radical initiators.

The suspension polymerization reaction is effected by dispersing styrene in water inside a reactor (e.g. autoclave). The reactor is typically equipped with a stirring system, a heating system of the polymerization mixture and a cooling system for removing the heat formed during the reaction.

The reaction mixture generally comprises styrene and water in a styrene:water weight ratio within the range of 0.5:1-1:0.5.

In order to favour the dispersion of styrene in the water and/or avoid coalescence phenomena between the polymer particles, the polymerization mixture can comprise suspending agents, such as inorganic salts of phosphoric acid (e.g. calcium triphosphate) and/or anti-caking agents, such as surfactants (e.g. dodecylbenzenesulfonate), polyvinyl alcohol, and polyvinylpyrrolidone.

The suspending agents are generally present in the polymerization mixture in an overall quantity ranging from 0.001% to 1% by weight with respect to the weight of the polymerization mixture, said quantity also being selected in relation to the dimensions of the reactor and relative fluid-dynamics.

The anti-caking agents are generally present in the polymerization mixture in an overall quantity ranging from 0.1 to 1,000 ppm by weight with respect to the weight of the polymerization mixture.

Peroxide compounds, such as benzoylperoxide, tert-butylperoxy-2-ethylhexanoate and tert-butylperbenzoate, can be used, for example, as radical initiators.

Each radical initiator is generally present in the polymerization mixture in a quantity ranging from 0.05 to 1.0% by weight with respect to the weight of the polymerization mixture.

In order to obtain expandable polymer beads, the polymerization mixture also comprises at least one expanding agent. Examples of expanding agents are: aliphatic or cycloaliphatic hydrocarbons containing from 3 to 6 carbon atoms (e.g. n-pentane, iso-pentane, cyclopentane), halogenated derivatives of aliphatic hydrocarbons containing from 1 to 3 carbon atoms (e.g. dichlorodifluoromethane, 1,2,2-trifluoroethane, 1,1,2-trifluoroethane), carbon dioxide, water and ethyl alcohol.

The expanding agent is generally present in the polymerization mixture in a quantity ranging from 2 to 10% by weight with respect to the weight of the polymerization mixture.

The polymerization mixture can also comprises chain transfer agents, expansion adjuvants, nucleating agents, plasticizers, etc.

In a preferred embodiment, the polymerization reaction is carried out in the presence of at least two peroxide initiators, the first active at a first temperature (e.g. 85-95° C.), the second active at a second temperature, higher than the above first temperature (e.g. 110-140° C.)

In this embodiment, the polymerization mixture is initially heated to the temperature at which the first initiator is active (e.g. about 90° C.) and kept at this temperature until the so-called "zero separation" point is reached.

The "zero separation" point corresponds to the point in which the density of the polymer which has been formed in the polymerization mixture is substantially equal to that of the water. After reaching the "zero separation" point, the temperature of the polymerization mixture is raised to the temperature at which the second initiator is active (e.g. about 115° C.) and then kept at this temperature until the polymerization reaction has been completed.

The expanding agent can be added to the polymerization mixture from the beginning together with the styrene monomer or during the reaction, for example when the "zero separation" point has been reached.

During the reaction, within the polymerization mixture, particles of EPS (beads) are formed, which increase in size as the reaction progresses. The growth of the particles can be regulated, for example, by adding more or less high quantities of dispersing agents and/or anti-caking agents, which prevent the particles from coalescing with each other.

At the end of the reaction, the EPS beads are separated from the reaction mixture and subjected to washing, in order to eliminate the residues of reaction mixture, and drying.

The final product consists of EPS beads having a substantially spherical form and an average diameter generally ranging from 0.2 to 2 mm, preferably from 0.5 to 1.0 mm.

In order to apply the method according to the present invention to the monitoring of a control parameter of a synthesis reaction of EPS, such as, for example, the above size of polymer beads, it is necessary to have a calibration curve capable of correlating a NIR reflectance spectrum of a polymerization reaction mixture of EPS with the values of this control parameter.

The calibration curve can be prepared with methods known to a skilled person in the field. The calibration curve is preferably obtained with univariate regression methods or, more preferably, by means of chemometric multivariate regression methods.

In order to obtain the calibration curve, for example, a plurality of sample polymerization mixtures (also indicated hereafter as "batch samples") can be prepared, each of which is subjected to polymerization according to the same pre-established temperature profile.

For the purposes of the present invention, temperature profile refers to the time sequence of the raising and lowering phases of the temperature of the polymerization mixture and relative maintenance periods of said mixture at each temperature. The temperature profile used for obtaining the calibration curve is preferably that used for the same polymerization reaction in the production process to which the monitoring method according to the present invention is to be applied.

In general, the greater the number of batch samples used for preparing the calibration curve, the more accurate the determination of the control parameter will be during the polymerization reaction subjected to monitoring.

The number of batch samples is generally selected in relation to the number of variables that can influence the control parameter to be monitored.

The number of batch samples used for defining the calibration curve is preferably equal to at least 5, more preferably at least 10. In a particularly preferred embodiment, the number of batch samples ranges from 10 to 50.

A plurality of NIR reflectance spectra is acquired on each batch sample in order to obtain the calibration curve. Each of said spectra is acquired at a different advancement degree of the polymerization reaction.

The value of the control parameter(s) is determined in correspondence with the acquisition of each NIR spectrum, using a reference measurement method.

For the purposes of the present invention, a reference measurement method is a measurement method, different from that of the present invention, which allows the value of the control parameter of interest to be determined on the polymerization mixture. For the purposes of the present invention, the value determined with the reference method is also indicated as "reference value" of the parameter.

Basically, methods known in the art commonly used for the monitoring of control parameters of polymerization reactions in heterogeneous phase can be substantially used as reference methods. The reference method used is preferably a method which allows the value of the control parameter to be determined with a low margin of uncertainty.

In the case of the average particle size of the polymer, the reference value can be determined by subjecting, for example, the polymerization mixture to the following analyses: acoustic spectroscopy, spectrophotometry (e.g. laser diffraction, dynamic light scattering) and image analysis.

The reference value of the average size of the polymer particles can also be obtained by visually comparing the polymer particles present in the polymerization mixture with standard samples of particles of the same polymer having known dimensions.

The reference method for determining the average particle size is preferably acoustic spectroscopy, more preferably ultrasonic spectroscopy.

When the control parameter is the conversion percentage of a reference monomer present in the polymerization mixture (in the case of EPS, the styrene monomer) said parameter can be determined, for example, by means of refraction index analysis or thermogravimetric analysis of the polymerization mixture according to techniques known in the art.

The determination of the control parameter with the reference method can, for example, be effected by taking an aliquot of the batch sample of which the NIR spectrum has been acquired and subjecting it to an off-line measurement of the control parameter. The determination of the control parameter with the reference method can also be effected by means of on-line and in-line measurement methods.

As already specified, the NIR spectra used for the calibration are acquired on each batch sample at different advancement degrees of the polymerization reaction. The advancement degree, hereinafter also indicated as "reaction time", is the period of time that has elapsed between the beginning of the polymerization (time "zero") and a given moment during the reaction (for example, the moment of acquisition of a NIR spectrum).

In the case of the synthesis of EPS described above, the beginning of the polymerization is generally associated with reaching the lowest temperature at which one of the radical initiators present in the polymerization mixture is active.

The reaction times at which the NIR spectra of a first batch sample are acquired can be the same as a second or further batch sample or different.

In the case of the synthesis of EPS, in a preferred embodiment, the NIR spectra and the determinations of the control parameter (e.g. average particle size) with the reference method are effected, for all the batch samples, at the temperature at which the first radical initiator is active (e.g. 90° C.) and at different conversion percentages of the styrene monomer (for example: 10%, 30%, 50% and 65% of conversion).

In accordance with the present invention, in preparing the calibration curve, it is generally preferable to acquire the NIR spectra and determine the corresponding reference values of the control parameter of interest on a series of batch samples wherein the polymerization is carried out under such conditions that the value of said parameter is substantially independent of the conversion degree of the reference monomer.

In particular, in the case of the monitoring of the average particle size of EPS, the polymerization reaction is preferably carried out in each of the batch samples under such conditions that, with the same conversion degree of the monomer, each of the batch samples contains particles of EPS having different dimensions.

For the suspension synthesis of EPS, it has been observed that the particle size mainly depends on the stirring degree of the polymerization mixture and quantity of suspending agent, whereas the conversion percentage of the styrene monomer mainly depends on the temperature profile adopted for the reaction and the quantity of radical initiator.

In the case of EPS, the above condition of independence of the particle size from the conversion degree can therefore be obtained by stirring the batch samples with a different intensity and/or using different concentrations of suspending agents and/or anti-caking agents.

The NIR spectra, both for obtaining the calibration curve (calibration spectra) and for determining the control parameter in the application of the method according to the present invention (measurement spectra), are preferably acquired within the range of wavenumbers 4,000-15,000 cm$^{-1}$, preferably within the range of 6,000-10,000 cm$^{-1}$.

The NIR calibration and measurement spectra are acquired in-line, using a NIR reflection probe of the type known in the art, for example as previously described with reference to FIGS. 1 and 2 enclosed. For this purpose, the probe can be connected, for example, to a Fourier transform or to a diode array spectrophotometer.

The light radiation reflected from the sample analyzed and collected by the detection system can be advantageously processed, according to the techniques known to experts in the field, in the form of absorption spectrum (A) in relation to the wavenumber (cm$^{-1}$) of the incident radiation. The absorption (A) is calculated starting from the reflectance value (R) measured on the basis of the relation A=log (1/R).

Once acquired, the calibration and measurement spectra can be pre-processed with methods known in the art in order to correct any possible spectral distortions due for example to shifts of the base line.

The calibration spectra and reference values of the particle sizes of EPS (determined with the reference measurement method) are analyzed with known univariate and/or multivariate linear regression mathematical-statistical methods in order to determine a mathematical correlation (calibration curve) between the spectroscopic characteristics of the NIR spectra and the values of the average dimensions of the polymer particles.

The multivariate linear regression method is preferably selected from: multiple least-square method, partial least-square method, method of the main components and combinations thereof.

The calibration curve resulting from the application of the above multivariate regression methods can be represented, for example, by the equation:

$$P=K_0+K_1 L(\lambda_1)+K_2 L(\lambda_2)+ \ldots +K_n L(\lambda_n),$$

wherein P is the value of the control parameter,
$K_{0, 1, 2, \ldots, n}$ are the linear regression coefficients and $L(\lambda_1), L(\lambda_2), \ldots, L(\lambda_n)$ are the absorbance values (L) at the wavelength $\lambda_n$, or other value derivable from the absorbance.

The calibration curve obtained from the multivariate regression analysis is subsequently subjected to validation using a series of control batch samples prepared analogously to the batch samples used for the calibration curve and subjected to polymerization according to the same temperature profile adopted for the same.

Once validated, the calibration curve can be used for calculating the value of the control parameter (e.g. average size of the polymer particles), by applying it to a NIR spectrum acquired in-line on a polymerization mixture of which the evolution of said parameter during the reaction is to be monitored.

In another preferred embodiment, the method of the present invention can be used for monitoring the conversion degree of a reference monomer during a polymerization reaction in heterogeneous phase.

For this purpose, the calibration curve is constructed by correlating the values of the conversion percentage of the reference monomer, measured with a reference method, with the corresponding NIR spectra acquired in-line on the same batch samples.

The preparation of the batch samples, the acquisition of the spectra and corresponding reference measurements of the control parameter and the mathematical-statistical treatment of the data collected for obtaining the calibration curve are the same as those previously described for monitoring the particle size.

In the case of the synthesis of EPS, the monitoring of the conversion degree of a reference monomer (i.e. styrene monomer) is particularly important for determining both the attainment of the "zero separation" point and also the completion of the reaction and consequently the moment for proceeding with the recovery of the reaction products.

In this respect, it should be noted that in some cases it may be difficult or even impossible to measure reference values of a control parameter under the same acquisition conditions of the NIR spectra. In the case of the synthesis of EPS, for example, NIR reflectance measurements can also be effected when the reaction mixture is at a temperature of about 200° C., whereas reference values of the conversion degree cannot be obtained at the same temperature, as samples of the polymerization mixture cannot be collected from the reactor at temperatures generally higher than approximately 90° C.

In these cases, a calibration curve which adequately predicts the values of the control parameter can only be obtained at a low temperature, i.e. within the temperature range at which the NIR calibration spectra were acquired and at which the samples to be subjected to analysis with the reference measurement method could be collected, whereas at temperatures higher than the maximum limit of said range, the value of the control parameter predicted can deviate—in absolute terms—even significantly from the actual value.

The method, object of the present invention, however, in any case advantageously allows the maximum conversion point of the reference monomer to be identified with a good approximation. When the polymerization reaction approaches the maximum conversion point, in fact, it can be observed that the value predicted for the conversion percentage through the application of the calibration curve, even if it has significantly deviated from the actual value (generally higher than a 100% conversion value), it reaches in any case a maximum value which remains constant with time. Reaching this maximum value is therefore an index of having reached the maximum conversion degree of the reaction.

The following embodiment example is provided for further illustrating the invention.

EXAMPLE 1

In the case of a synthesis reaction of EPS in aqueous suspension, 13 batch samples were prepared for setting up a calibration curve.

Each batch sample subjected to polymerization contained:
water and styrene monomer in a weight ratio equal to 1:1 (3.5 kg each);
benzoylperoxide (peroxide initiator active at 85-95° C.), 0.4% with respect to the total weight of the polymerization mixture;
tert-butylperbenzoate (peroxide initiator active at 110-120° C.), 0.2% with respect to the total weight of the polymerization mixture;
calcium triphosphate (suspending agent), 0.02% with respect to the total weight of the polymerization mixture;
Na dodecylbenzenesulfonate (anti-caking agent) 20 ppm with respect to the total weight of the polymerization mixture;
pentane (expanding agent), 8.5% by weight with respect to the total weight of the polymerization mixture.

For all the batch samples, the polymerization reaction was carried out at 90° C. for 3.5 hours and was then continued at 115° C. (temperature rise rate 0.5° C./min) for 4.5 hours. Each polymerization reaction was effected in an autoclave having a capacity of 8 liters, equipped with a stirring system and a heating and cooling system of the polymerization reaction.

At the end of the reaction, the reaction mixture was cooled and the beads of EPS were separated, washed with water and dried.

During the reaction, the batch samples were kept under stirring by means of a blade stirrer, whose rate was set at a value ranging from 180 to 220 revs/minute (rpm).

The concentration of calcium triphosphate of each batch sample was selected within the range of 0.01-1% with respect to the weight of the polymerization mixture.

Each of the 13 batch samples was characterized by a different combination of stirring rate and calcium triphosphate values, so as to have, with the same conversion degree, a different average size value of the beads. In this way, the dimension of the beads was substantially prevented from depending on the advancement degree of the reaction.

5 or 6 NIR spectra were acquired for each batch sample at a temperature of 90° C. for a total of 60 spectra. The spectra were acquired in correspondence with the following conversion percentages of styrene monomer: 10%, 30%, 50% and 65%.

The spectra were acquired by means of a NIR reflection spectra probe (Model GLADIUS of the company Hellma), by putting the sampling window in contact with the polymerization mixture. The probe was introduced transversally with respect to a wall of the autoclave, so as to have an internal surface of the sampling window substantially aligned with the internal surface of the wall of the autoclave.

A NIR Fourier transform spectrophotometer (BRUKER MATRIX F) was used for the acquisition of the spectra. The processing of the spectra for the calibration took into consideration the frequency range of 9,400-6,000 $cm^{-1}$.

The corresponding particle-size value was determined on the batch samples subjected to the NIR spectra measurements, using, as reference method, a visual comparison of a sample collected from each of said batch samples with a series of 10 reference samples of EPS beads having known dimensions ranging from 0.1 mm to 1.7 mm.

The calibration curve was obtained by applying a multivariate linear regression method based on the partial least square method, identifying 8 main components. The calibration curve was validated by means of cross-validation, obtaining an average square error equal to 0.05 mm.

Figure 3:
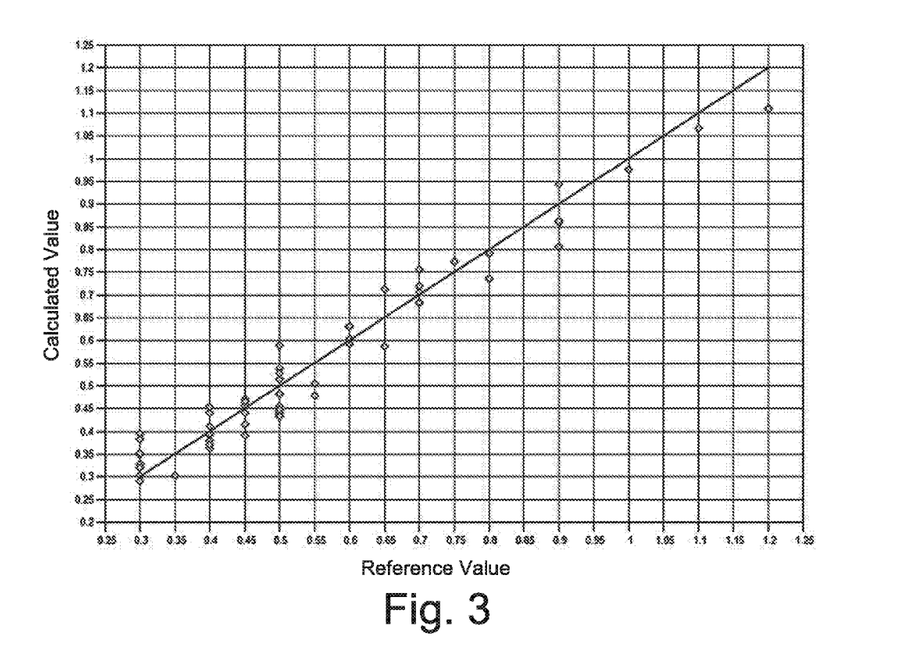
FIG. 3 shows the correlation graph between reference value (abscissa) and calculated value by means of the calibration curve (ordinate).

FIG. 3 shows the correlation graph between reference value (abscissa) and calculated value by means of the calibration curve (ordinate).

Figure 4:
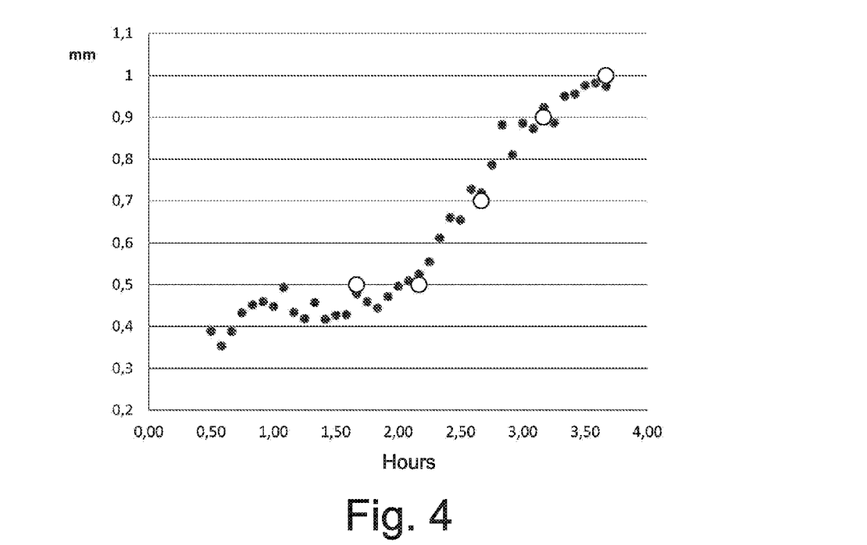
FIG. 4 shows a prediction graph of the value of the average particle size (in mm) with respect to the reaction time obtained by applying the calibration curve, in which: the full circles (●) indicate the estimated value of the parameter; the empty circles (○) indicate the value determined with the reference method.

FIG. 4 shows a prediction graph of the value of the average particle size (in mm) with respect to the reaction time obtained by applying the calibration curve, in which: the full circles (●) indicate the estimated value of the parameter; the empty circles (○) indicate the value determined with the reference method.

The results show that the method according to the present invention is sensitive to a variation in the average particle sizes and therefore suitable for effectively and reliably monitoring their growth during the polymerization reaction.

Furthermore, the polymerization cycles of the batch samples were effected in the same autoclave without the necessity of any cleaning or maintenance intervention of the probe.

Figure 5:
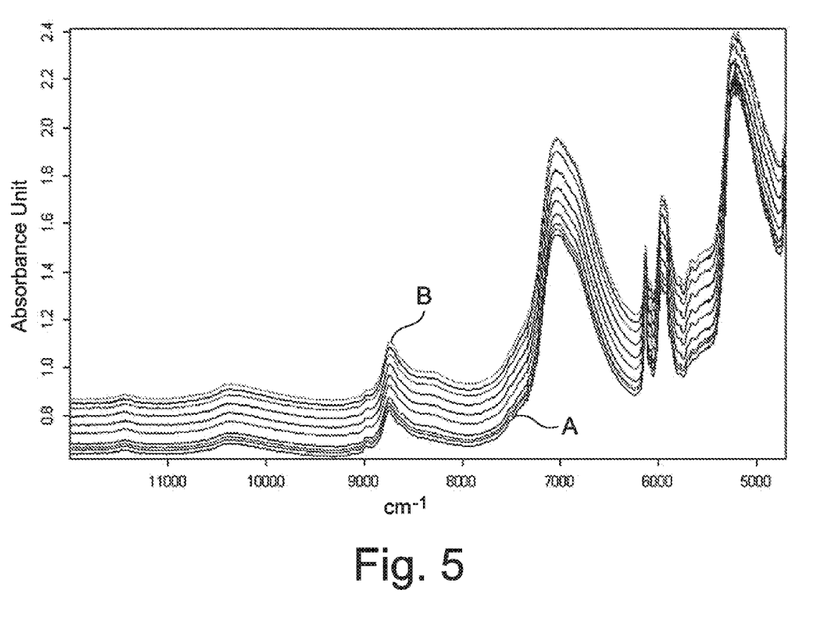

After validation of the calibration, the method was used for continuously monitoring the growth of the EPS beads during the polymerization. FIG. 5 shows some of the NIR spectra measured in-line during the polymerization reaction, in which the raising of the spectral base line linked to an increase in the average dimensions of the EPS beads, passing from about 300 micrometers (spectrum A below) to about 1.2 mm (spectrum B above), can be clearly seen.

The invention claimed is:

1. A method for monitoring a control parameter of a polymerization reaction mixture in heterogeneous phase comprising:
    (a) acquiring at least one NIR reflectance spectrum of said mixture;
    (b) calculating a value of said control parameter by means of a calibration curve which correlates the NIR reflectance spectrum with the values of said control parameter measured with a reference measurement method, wherein said control parameter is the average size of the polymer particles which are formed during said polymerization reaction, and wherein said average particle size is within the range of 100 μm-3 mm.

2. The method according to claim 1, wherein said polymerization reaction is a polymerization reaction of one or more monomers selected from α-olefins having general formula $R_1R_2C=CH_2$, wherein:
    $R_1$ is hydrogen or methyl;
    $R_2$ is a group selected from: $C_1$-$C_{10}$ alkyl, $C_1$-$C_6$ aryl possibly substituted with one or more groups selected from halogen, $C_1$-$C_4$ alkyl and $C_1$-$C_4$ alkoxyl.

3. The method according to claim 2, wherein said polymerization reaction is a synthesis reaction of polystyrene in aqueous suspension.

4. The method according to claim 1, wherein said reference measurement method is selected from: acoustic spectroscopy, spectrophotometry, image analysis and visual comparison of said polymer particles with standard samples of particles of the same polymer having known dimensions.

5. The method according to claim 1, wherein said control parameter is the conversion degree of at least one monomer of the polymerization mixture.

6. The method according to claim 5, wherein said reference measurement method is selected from refraction index analysis or thermogravimetric analysis.

7. The method according to claim 1, wherein said calibration curve is obtained by correlating, by means of a multivariate linear regression method, a plurality of NIR reflectance spectra with a corresponding plurality of values of said control parameter; said spectra being acquired on a series of sample polymerization mixtures at different advance degrees of the polymerization reaction; said values of said control parameter being measured on said sample polymerization mixtures with a reference measurement method.

8. The method according to claim 1, wherein said multivariate linear regression method is selected from: multiple least-squares method, partial least-squares method, method of the main components and combinations thereof.

9. The method according to claim 1, wherein said NIR reflectance spectra are acquired within the range of wavenumbers 4,000-15,000 $cm^{-1}$.

10. A method for the control of a polymerization reaction in heterogeneous phase which comprises the phase of monitoring at least one control parameter of said reaction according to claim 1.

11. An apparatus for implementing the method according to claim 1 comprising at least one polymerization reactor equipped with an acquisition system of NIR reflectance spectra comprising:
- at least one probe for irradiating a light radiation onto a polymerization reaction mixture contained in said reactor and substantially only collecting the radiation reflected from said mixture in response to said irradiation,
- at least one detection system optically coupled with said probe for detecting said radiation reflected,
- wherein said probe comprises at least one measurement head and at least one sampling window; said probe being included in a wall of said reactor, the internal surface of said sampling window being substantially aligned with the internal surface of said wall.

12. A method for monitoring a control parameter of a polymerization reaction mixture in heterogeneous phase comprising:
(a) acquiring at least one NIR reflectance spectrum of said mixture;
(b) calculating a value of said control parameter by means of a calibration curve which correlates the NIR reflectance spectrum with the values of said control parameter measured with a reference measurement method,
wherein said control parameter is the conversion degree of at least one monomer of the polymerization mixture and wherein said reference measurement method is selected from refraction index analysis or thermogravimetric analysis.

13. An apparatus for implementing the method according to claim 12, comprising at least one polymerization reactor equipped with an acquisition system of NIR reflectance spectra comprising:
- at least one probe for irradiating a light radiation onto a polymerization reaction mixture contained in said reactor and substantially only collecting the radiation reflected from said mixture in response to said irradiation,
- at least one detection system optically coupled with said probe for detecting said radiation reflected,
- wherein said probe comprises at least one measurement head and at least one sampling window; said probe being included in a wall of said reactor, the internal surface of said sampling window being substantially aligned with the internal surface of said wall.

* * * * *